United States Patent [19]

Plöger

[11] 4,117,086

[45] Sep. 26, 1978

[54] PROCESS OF STABILIZATION OF DIBASIC CALCIUM PHOSPHATE DIHYDRATE AGAINST HYDROLYSIS WITH 3-AMINO-1-HYDROXYPROPANE-1,1-DIPHOSPHONIC ACID

[75] Inventor: Walter Plöger, Hilden, Fed. Rep. of Germany

[73] Assignee: Henkel Kommanditgesellschaft auf Aktien, Düsseldorf-Holthausen, Fed. Rep. of Germany

[21] Appl. No.: 636,735

[22] Filed: Dec. 1, 1975

[30] Foreign Application Priority Data

Nov. 30, 1974 [DE] Fed. Rep. of Germany ....... 2456692

[51] Int. Cl.$^2$ ...................... C01B 15/16; C01B 25/26
[52] U.S. Cl. .................... 423/268; 423/308; 423/311; 424/57; 423/265
[58] Field of Search ................ 423/299–323, 423/265, 268; 424/49, 52, 57, 128

[56] References Cited

U.S. PATENT DOCUMENTS

| | | | |
|---|---|---|---|
| 2,018,410 | 10/1935 | McDonald et al. | 424/57 |
| 2,876,166 | 3/1959 | Nebergall | 424/52 |
| 3,012,852 | 12/1961 | Nelson | 23/109 |
| 3,066,056 | 11/1962 | Schlaeger et al. | 23/108 |
| 3,169,096 | 2/1965 | Schlaeger et al. | 424/57 |
| 3,244,478 | 4/1966 | Stahlheber | 423/311 |
| 3,308,029 | 3/1967 | Saunders et al. | 424/52 |
| 3,442,604 | 5/1969 | Smith et al. | 23/108 |
| 3,488,419 | 1/1970 | McCune et al. | 424/49 |
| 3,678,154 | 7/1972 | Widder et al. | 424/52 |
| 3,792,152 | 2/1974 | Kim | 423/311 |

FOREIGN PATENT DOCUMENTS 2,130,794  1/1973  Fed. Rep. of Germany ........... 423/311

*Primary Examiner*—O. R. Vertiz
*Assistant Examiner*—Gregory A. Heller
*Attorney, Agent, or Firm*—Hammond & Littell

[57] ABSTRACT

A process for stabilizing dibasic calcium phosphate dihydrate against hydrolysis comprising treating an aqueous suspension of dibasic calcium phosphate dihydrate at a pH of from 5 to 10 with 3-amino-1-hydroxypropane-1,1-diphosphonic acid, or a water-soluble salt thereof, in an amount of from 0.01 to 5% by weight with reference to the dibasic calcium phosphate dihydrate; as well as tooth cleaning preparations containing the stabilized dibasic calcium phosphate dihydrate.

5 Claims, No Drawings

PROCESS OF STABILIZATION OF DIBASIC CALCIUM PHOSPHATE DIHYDRATE AGAINST HYDROLYSIS WITH 3-AMINO-1-HYDROXYPROPANE-1,1-DIPHOSPHONIC ACID

RELATED ART

Dibasic calcium phosphate dihydrate having the formula $CaHPO_4.2H_2O$ is a polishing substance frequently utilized in tooth cleaning preparations as, for example, toothpastes and powders. For this purpose it may be used alone or in admixture with other polishing substances as, for example, silica gel or plastics cleaning substances. Besides having some properties advantageous for this purpose, however, the calcium-hydrogenphosphate-dihydrate has the disadvantage that it is not stable to aqueous hydrolysis. This lack of stability to hydrolysis has a particularly aggravating effect in preparations containing water as, for example, toothpastes. However, also in products such as tooth powders it may lead to undesired results. In the presence of moisture, dibasic calcium phosphate dihydrate hydrolyzes easily with liberation of acid, in which case basic phosphates are formed, which mostly have an apatite structure. The processes which thereby take place may be theoretically represented by the following empirical reaction:

$$5CaHPO_4 + H_2O \rightarrow Ca_5(OH)(PO_4)_3 + 2H_3PO_4$$

In this reaction the dihydrate water of crystallization has been disregarded. The speed as well as the end point of this reaction is influenced by several circumstances such as temperature, pH of the mixture and its composition. The temperature has a particularly great influence, since the dibasic calcium phosphate dihydrate decomposes at temperatures as low as from 36° C. with formation of anhydrous dibasic calcium phosphate, hydroxyapatite, phosphoric acid and water, or respectively, some calcium phosphate solution. Consequently, the possibility results that even toothcleaning preparations produced without addition of water can hydrolyze. Temperatures of 36° C. and over, moreover, may easily occur in the making of the preparations containing dibasic calcium phosphate dihydrate or, for example, in the storage of finished products, especially in tropical zones.

The acid liberated in the hydrolysis not only, in some cases, alters the pH value of the mixture, but it may change the whole structure of the product; for example, it may cause a paste to solidify; powders may stick together or agglomerate, and tablets may disintegrate. If, in addition to the dibasic calcium phosphate dihydrate, carbonates are present in the mixture, as may be the case with tooth cleaning preparations, during the hydrolysis evolution of carbon dioxide occurs as a very unpleasant side phenomenon, which in some cases may lead to bursting of the container, as for example, tubes, or at least to an expansion or bulge.

For the use of a polishing agent as cleaning material in toothcleaning preparations, its abrasive behavior is of decisive importance, since products to be used for this purpose must only have an abrasive power which does not cause damage to the teeth. Owing to its favorable abrasive behavior, dibasic calcium phosphate dihydrate already enjoys great popularity as a cleaning material in tooth cleaning preparations. If, however, a conversion into the substantially harder apatite is caused by the hydrolysis, in some circumstances abrasive agents or agents with uncontrolled abrasive power may be formed.

Therefore, earlier attempts have already been made to stabilize dibasic calcium phosphate dihydrate against hydrolysis, in order to made possible its use in tooth cleaning agents without any problems. For this purpose various compounds such as pyrophosphoric acid, sodium/calcium pyrophospate or sodium pyrophosphate have been added to a suspension of dibasic calcium phosphate dihydrate in water; the suspension was then filtered and the product obtained was incorporated in the tooth cleaning preparations. All these stabilizing compounds were not satisfactory, however, since in some cases complicated further treatments of the products were necessary in order to obtain a sufficient stability, and in other cases the process itself caused considerable technical difficulties.

It has further been proposed to use specific phosphonic acids, such as 1-hydroxyethane-1,1-diphosphonic acid or amino-tris-(methylenephosphonic acid) as stabilizers against hydrolysis of dibasic calcium phosphate dihydrate. These phosphonic acids as well as other phosphonic acids mentioned in this connection, however, have two essential disadvantages in respect to the stabilization of dibasic calcium phosphate dihydrate. Their stabilizing action still leaves much to be desired and the stabilization raises technical problems. Only products with the greatest possible long lasting inhibiting action are suitable for the use as stabilizer of dibasic calcium phosphate dihydrate for tooth cleaning preparations, since the inhibiting action of the phosphonic acids only lasts a certain time, and then usually stops suddenly. In the case of the already proposed phosphonic acids, the inhibiting action is not particularly great and does not last sufficiently long. Further, there is the disadvantage that the inhibiting action of the said phosphonic acids does not increase in every case with the increase of the amount added, but on the contrary falls off again, owing to which the desired dosing is technically difficult to carry out.

OBJECTS OF THE INVENTION

An object of the present invention is the development of a process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of a cyclic aminophosphonic compound selected from the group consisting of (A) 3-amino-1-hydroxypropane-1,1-diphosphonic acid, and (B) water-soluble salts thereof, and separating said stabilized dibasic calcium phosphate dihydrate.

Another object of the present invention is the obtaining of a stabilized dibasic calcium phosphate dihydrate.

A further object of the present invention is the obtaining of tooth cleaning preparations containing a stabilized dibasic calcium phosphate dihydrate.

These and other objects of the present invention will become more apparent as the description thereof proceeds.

DESCRIPTION OF THE INVENTION

It has now been found that a satisfactory and easily effected stabilization of dibasic calcium phosphate dihydrate against hydrolysis is possible by treating the dibasic calcium phosphate dihydrate in aqueous medium at a pH of from 5 to 10, preferably from 6 to 8, with 3-amino-1-hydroxypropane-1,1-diphosphonic acid, or a water-soluble salt thereof, in an amount of from 0.01 to 5% by weight, preferably from 0.03 to 2% by weight, referred to the amount of dibasic calcium phosphate dihydrate employed.

More particularly, the invention relates to a process for stabilizing dibasic calcium phosphate dihydrate against hydrolysis consisting essentially of suspending dibasic calcium phosphate dihydrate in an aqueous medium at a pH of from 5 to 10, containing from 0.01 to 5% by weight based on the content of said dibasic calcium phosphate dihydrate of a diphosphonic compound selected from the group consisting of (A) 3-amino-1-hydroxypropane-1,1-diphosphonic acid, and (B) water-soluble salts thereof, and separating said stabilized dibasic calcium phosphate dihydrate; as well as the stabilized dibasic calcium phosphate dihydrate so produced and tooth cleaning preparations containing the same.

In carrying out the process of the invention 3-amino-1-hydroxypropane-1,1-diphosphonic acid or its water-soluble salt, the dibasic calcium phosphate dihydrate, and water may be admixed in any manner. For example, 3-amino-1-hydroxypropane-1,1-diphosphonic acid or its water-soluble salt may be used in the mixture either as an aqueous solution or in solid form and the dibasic calcium phosphate dihydrate may be used in the mixture either as an aqueous suspension or in solid form.

The preparation of the 3-amino-1-hydroxypropane1,1-diphosphonic acid of the formula

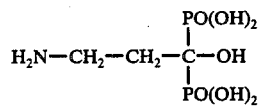

can be carried out in a simple way by reacting β-alanine or poly-β-alanine with a mixture of phosphorus trichloride and phosphorous acid in the presence or in the absence of an organic diluent, as is described in German Published Application (DAS) No. 2,130,794.

3-Amino-1-hydroxypropane-1,1-diphosphonic acid can also advantageously be used in the form of its water-soluble salts such as the alkali metal salts, especially lithium, sodium and potassium, and the ammonium salts. The conversion into the salts may easily be carried out by partial or complete neutralization with the corresponding bases.

The stabilization according to the present invention may either be carried out before isolation of the dibasic calcium phosphate dihydrate from the reaction medium in which it is prepared or in a later separate treatment process. The preparation of the dibasic calcium phosphate dihydrate may be effected according to processes known from the literature, for example, from calcium hydroxide and phosphoric acid.

If the stabilization is to be carried out on previously isolated dibasic calcium phosphate dihydrate which is the preferred method of production, this previously isolated dibasic calcium phosphate dihydrate is treated with an aqueous solution of the stabilizer, the pH of the solution being adjusted to from 5 to 10, preferably from 6 to 8. However, even if the stabilization is effected before isolation of the dibasic calcium phosphate dihydrate from the reaction medium, the aqueous suspension is set at a pH of 5 to 10, preferably 6 to 8, with the addition of the stabilizer. The amount of stabilizer required can easily be found by testing. It has been found that in general 0.01 to 5% by weight, preferably 0.03 to 2% by weight, based on the amount of dibasic calcium phosphate dihydrate to be stabilized is sufficient in the event no other stabilizers are present. The amount, within the indicated limits is dependent on (a) the extent of the desired stabilization, (b) the particle size, surface and surface structure of the dibasic calcium phosphate dihydrate prepared, and (c) the time of contact between the stabilizer and the product to be stabilized. It has further been found suitable to use the water-soluble salts of the cyclic aminophosphonic acids, as for example, alkali metal salts, especially sodium salts. If the free acids are to be used, it may be necessary to correct for pH deviations, for example, by addition of calcium hydroxide or calcium oxide. Owing to the small amounts of the added cyclic aminophosphonic acid, however, this is often unnecessary. The stabilizers to be used according to the present invention may also be used in combination with other substances, such as other stabilizers, aids to precipitation or protective colloids as, for example, with pyrophosphates, tripolyphosphates and other polymeric phosphates, polysilicates, polycarboxylates, lignin derivatives, gums and polysaccharides.

The present invention relates primarily to the preparation of a dibasic calcium phosphate dihydrate stabilized against hydrolysis, for use in tooth cleaning preparations. Such stabilized products, however, may also be advantageous in other fields of application. The tooth cleaning preparations to be prepared according to the present invention may contain, in addition to the stabilized dibasic calcium phosphate dihydrate serving as polishing material, the usual constituents such as, for example, thickeners, surface-active compounds or tensides, emulsifiers, bactericides, and flavoring substances. A toothpaste is the preferred form of the tooth cleaning preparations with a content of stabilized dibasic calcium phosphate dihydrate according to the present invention.

Toothpastes are generally pasty preparations based on water, which contain thickeners, wetting and foaming agents, moisture-retention agents, polishing, scouring or cleaning substances, aroma-imparting substances, taste correctors, antiseptic and other substances valuable as mouth cosmetics. The content of polishing substances in the toothpastes, i.e., the content of the dibasic calcium phosphate dihydrate which is to be used according to the present invention and which is stabilized against hydrolysis, will generally vary from 25 to 60% by weight, referred to the total mass of the toothpaste. The wetting and foaming agents employed are especially soap-free anionic surface-active compounds such as fatty alcohol sulfates, for example, sodium lauryl sulfate, monoglyceride sulfates, sodium lauryl sulfoacetate, sarcosides, taurides and other anionic surface-active compounds which do not affect the taste, in amounts from 0.5 to 5% by weight. For the preparation of the binder for toothpaste, all thickeners usual for this purpose may be used, such as hydroxyethylcellulose, sodium carboxymethylcellulose, tragacanth, carrageen moss, agar-agar and gum arabic, as well as additionally finely divided silicic acids, all in amounts of from 0.1 to 5% by weight of the whole toothpaste. As moisture-retention means, glycerine and sorbitol are of principal importance, in amounts which may be up to one-third or from 5 to 33⅓% by weight of the whole toothpaste. Water is also present in amounts of from 10 to 50% by weight of the whole toothpaste. With tooth powders, the water, thickeners and moisture-retention means are omitted. The desired aroma and taste requirements can be attained by an addition of essential oils such as peppermint, clove, wintergreen and sassafras oils, as well as by sweetening agents, such as saccharin, dulcin, dextrose and laevulose.

In addition, fluorine-containing compounds serving for the control of caries or for caries prophylaxis may be present. These are present in amounts of from 0 to 2% measured as fluorine ions of the whole tooth cleaning preparations. Such fluorine-containing compounds are, for example, sodium fluoride, potassium fluoride, aluminum fluoride, monoethanolamine-hydrofluoride, hexadecylaminehydrofluoride, oleylamine-hydrofluoride, N,N',N'-tri-(polyoxyethylene)-n-hexadecyl-propylenediamine-dihydrofluoride, bis-(hydroxyethyl)-amino-propyl-N-hydroxyethyl-octadecylamine-dihydrofluoride, magnesium aspartate-hydrofluoride, and tin fluoride. Also fluorine compounds in which the fluorine is present primarily in a preponderantly non-ionic bond, which, however, may split off fluoride, for example, by hydrolysis or other chemical reactions, such as sodium monofluorophosphate, potassium monofluorophosphate, magnesium monofluorophosphate, indium fluorozirconate, zirconium hexafluorogermanate, etc.

Optionally, further cleaning and filling substances possibly also used in the tooth cleaning preparations are present, as for example, plastics particles, silica gels or pyrogenic silicic acids.

The preparation of the dibasic calcium phosphate dihydrate stabilized against hydrolysis is generally effected by treatment of a previously isolated dibasic calcium phosphate dihydrate with an aqueous solution of the stabilizer. It is, of course, also possible to stabilize a dibasic calcium phosphate dihydrate present in an already finished toothpaste subsequently against the reaction with fluorine ions by an addition thereto of salts of 3-amino-1-hydroxypropane-1,1-diphosphonic acid. Such measures may be introduced in special circumstances, but these should remain restricted to exceptions, since the result of such a difficultly controllable treatment in a system as heterogeneous as that represented by a toothpaste is not always completely ensured.

The following examples further illustrate the present invention without, however, being restricted thereto.

EXAMPLES

First, the preparation of 3-amino-1-hydroxypropane-1,1-diphosphonic acid to be used as a stabilizer according to the present invention is described.

Preparation of
3-amino-1-hydroxypropane-1,1-diphosphonic acid 206 gm (1.5 mols) of phosphorus trichloride are slowly dropped while stirring into a mixture heated in a boiling water bath of 89.1 gm (1 mol) of β-alanine, 123 gm (1.5 mols) of phosphorous acid, and 500 ml of chlorobenzene, and heating on the boiling water bath is continued for a further 3 hours. During this time the contents of the flask become solid. After the reaction is finished, 600 ml of water are added and the product is heated for a short time, treated with animal charcoal and filtered while hot. The 3-amino-1-hydroxypropane-1,1-diphosphonic acid gradually crystallizes out from the aqueous phase in a cooling cabinet. The mother liquor is concentrated and treated with methanol, whereupon still further diphosphonic acid is precipitated. The 3-amino-1-hydroxypropane-1,1-diphosphonic acid is then recrystallized from water.

The following examples serve to prove the superior activity of the 3-amino-1-hydroxypropane-1,1-diphosphonic acid to be used as a stabilizer according to the present invention. The products thus stabilized according to the present invention were not only compared with untreated dibasic calcium phosphate dihydrate, but also with products which were obtained by treatment with other structurally different phosphonic acids.

As a measure of the stabilizing action, the hydrolysis of the dibasic calcium phosphate dihydrate in an aqueous suspension was followed at 60° C. The acid continuously formed during the hydrolysis was back-titrated with alkali, owing to which a constant pH value of the hydrolysis solution was ensured during the whole hydrolysis. The consumption of alkali was continuously followed over the entire period and consequently gave at each point of time a measure for the progress of the hydrolysis. The alkali consumption may also be indicated as a percentage of the final consumption, which then corresponds to the percentage rate of phosphate which is hydrolyzed at the respective point of time. The titration over the given time may advantageously be carried out by means of a recording autotitrator, which is adjusted for pH-stat measurements.

In order to be able to compare the individual experiments truly, it is not only necessary in the measurements to keep constant, for example, the parameters of temperature, pH, amount of dibasic calcium phosphate dihydrate, and the solution, but the same dibasic calcium phosphate dihydrate should also always be used. This requirement was fulfilled in the present case in that, according to the directions of Jensen and Rathlev (in Bailor, "Inorganic Syntheses," Vol. 4, New York-Toronto-London, 1953, pp. 1/218, 20), a large quantity of well crystallized dibasic calcium phosphate dihydrate was prepared and the fraction of particle size between 0.5 and 1 mm was sieved out and employed in the following.

EXAMPLE 1

13.6 mg of 3-amino-1-hydroxypropane-1,1-diphosponic acid (0.136%, based on the $CaHPO_3.2H_2O$ employed) were dissolved in 10 ml of water. The solution was adjusted with a solution of sodium hydroxide to a pH of 7.5 and made up to 25 ml with water. 15 ml of barbital buffer of pH 7.5 were added to this. Then 10 gm of dibasic calcium phosphate dihydrate were suspended in this solution, left for 24 hours therein, then filtered off by suction, washed with some water and alcohol and dried.

In the same way dibasic calcium phosphate dihydrates were prepared which had been treated respectively with 37 mg (0.37%, based on the $CaHPO_4.2H_2O$) of the following phosphonic acids:
  1-hydroxyethane-1,1-diphosphonic acid
  N-methylaminomethanediphosphonic acid
  N,N-dimethylaminomethanediphosphonic acid
  2-phosphonopropane-1,2-dicarboxylic acid
  amino-tris-(methylene-phosphonic acid).
A similar sample was also made without addition of phosphonic acid.

2.58 gm of each of these treated dibasic calcium phosphate dihydrates were mixed in a temperature controlled vessel with 3 ml of a barbital buffer solution of pH 7.6 and 7 ml of water. To this was added a mixture heated to about 80° C. of 7 ml of barbital buffer pH 8 and 33 ml of water. A $CaHPO_4.2H_2O$ suspension at 60° C. and a pH of 7.5 was obtained. The pH of the suspension was kept constant by means of an automatic titrator by addition of NaOH and the consumption of alkaline liquor caused by the hydrolysis was recorded over the entire hydrolysis period.

The following times of hydrolysis resulted for the individual samples, which are shown in the following Table 1.

TABLE 1

| Inhibitor | | Time for x % Hydrolysis (Minutes) | | | | | |
|---|---|---|---|---|---|---|---|
| | | 10% | 20% | 40% | 60% | 80% | 100% |
| 0.136% | 3-amino-1-hydroxy-propane-1,1-diphosphonic acid | 105 | 122 | 137 | 139 | 143 | 155 |
| 0.37% | 1-hydroxyethane-1,1-diphosphonic acid | 30 | 32 | 35 | 39 | 42 | 52 |
| 0.37% | N-methylaminomethane-diphosphonic acid | 65 | 68 | 71 | 73 | 74 | 80 |
| 0.37% | N,N-dimethylamino-methanediphosphonic acid | 19 | 21 | 23 | 26 | 31 | 43 |
| 0.37% | 2-phosphonopropane-1,2-dicarboxylic acid | 7 | 8 | 11 | 16 | 24 | 35 |
| 0.37% | amino-tris-(methylene-phosphonic acid) | 15 | 17 | 20 | 24 | 28 | 35 |
| | Without addition | 7.5 | 7.8 | 8.0 | 8.2 | 8.3 | 9.4 |

These measured values show clearly that the phosphonic acid claimed is substantially more active than the substances compared although it was only used in half the amount.

EXAMPLE 2

Dibasic calcium phosphate dihydrates were prepared and measured as in Example 1, which were treated with the amounts of the respective inhibitors indicated in Table 2. Hydrolysis was effected and measured as in Example 1. The results obtained are to be taken from the following Table 2.

TABLE 2

| Inhibitor | | Time for x % Hydrolysis (Minutes) | | | | | |
|---|---|---|---|---|---|---|---|
| | | 10% | 20% | 40% | 60% | 80% | 100% |
| 0.75% | 3-amino-1-hydroxypropane-1,1-diphosphonic acid | 500 | 640 | 1010 | 1035 | 1038 | 1045 |
| 0.75% | N-methylpyrrolidone-5,5-diphoshonic acid | 11 | 12 | 14 | 18 | 24 | 40 |
| 0.75% | 2-phosphonobutane-1,2,4-tricarboxylic acid | 13 | 14 | 17 | 23 | 30 | 38 |
| 0.75% | ethylenediamine-tetra-(methylenephosphonic acid) | 56 | 60 | 65 | 68 | 72 | 80 |
| 0.75% | amino-tris-(methylene-phosphonic acid) | 15 | 17 | 20 | 24 | 28 | 35 |

At the same concentration used the 3-amino-1-hydroxypropane-1,1-diphosphonic acid according to the present invention in this series of experiments showed its superior action.

EXAMPLE 3

A $CaHPO_4.2H_2O$ cleaning material already stabilized by known means and commerically obtainable was treated according to the process described in Example 1 additionally with 0.75% of 3-amino-1-hydroxypropane-1,1-diphosphonic acid according to the present invention and the hydrolysis was measured. The additional stability to hydrolysis resulting therefrom is compared with a sample not additionally treated and with a sample which was treated with a phosphonic acid already known for this purpose. It is shown that the compound according to the present invention gives a distinct additional inhibition, which is far superior to that of already known compounds. The values obtained by the measurements are given in the following Table 3.

TABLE 3

| | Additional Inhibitor | Time for 100% Hydrolysis (Minutes) |
|---|---|---|
| | Without addition | 140 |
| 0.75% | amino-tris-(methylene-phosphonic acid) | 185 |
| 0.75% | 3-amino-1-hydroxypropane-1,1-diphosphonic acid | 1590 |

In the following examples formulations for tooth cleaning preparations are given which contain dibasic calcium phosphate dihydrate stabilized according to the present invention as a polishing material.

EXAMPLE 4

Composition of a toothpaste according to the present invention.

| | Parts by weight |
|---|---|
| Glycerine | 30.0 |
| Water | 18.0 |
| Sodium carboxymethylcellulose | 1.0 |
| Dibasic calcium phosphate dihydrate stabilized with 1% of 3-amino-1-hydroxypropane-1,1-diphosphonic acid | 36.0 |
| Insoluble sodium metaphosphate | 10.0 |
| Sodium lauryl sulfate | 1.0 |
| Pyrogenic silicic acid | 1.5 |
| Sodium monofluorophosphate | 0.5 |
| Essential oils | 1.5 |
| Saccharin sweetener | 0.5 |

EXAMPLE 5

Composition of a toothpowder according to the present invention.

|  | Parts by weight |
|---|---|
| Dibasic calcium phosphate dihydrate stabilized with 1% of 3-amino-1-hydroxypropane-1,1-diphosphonic acid | 50.0 |
| Precipitated chalk | 30.0 |
| Finely divided silicic acid | 10.0 |
| Milk sugar | 4.0 |
| Precipitated magnesium carbonate | 4.0 |
| Titanium dioxide | 1.0 |
| Tannin | 1.0 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of a diphosphonic compound selected from the group consisting of (A) 3-amino-1-hydroxypropane-1,1-diphosphonic acid, and (B) water-soluble salts thereof, and separating said stabilized dibasic calcium phosphate dihydrate.

2. The process of claim 1 wherein said pH is between 6 and 8.

3. The process of claim 1 wherein the amount of said cyclic aminophosphonic acid compound is from 0.03% to 2% by weight based on the content of said dibasic calcium phosphate dihydrate.

4. The process of claim 1 wherein said water-soluble salts are selected from the group consisting of the alkali metal salts and ammonium salts.

5. A dibasic calcium phosphate dihydrate stabilized against hydrolysis by 3-amino-1-hydroxypropane-1,1-diphosphonic acid produced by the process of suspending dibasic calcium phosphate dihydrate in an aqueous medium at a pH of from 5 to 10, containing from 0.01% to 5% by weight based on the content of said dibasic calcium phosphate dihydrate of a diphosphonic compound selected from the group consisting of (A) 3-amino-1-hydroxypropane -1,1-diphosphonic acid, and (B) water-soluble salts thereof, and separating said stabilized dibasic calcium phosphate dihydrate.

* * * * *